(12) United States Patent
Kirschen et al.

(10) Patent No.: US 8,967,809 B2
(45) Date of Patent: Mar. 3, 2015

(54) METHODS AND SYSTEMS FOR INTELLIGENT VISUAL FUNCTION ASSESSMENTS

(75) Inventors: David Gary Kirschen, Brea, CA (US); Daniel Moses Laby, Canton, MA (US)

(73) Assignee: Alcon Research, Ltd., Fort Worth, TX (US)

( * ) Notice: Subject to any disclaimer, the term of this patent is extended or adjusted under 35 U.S.C. 154(b) by 148 days.

(21) Appl. No.: 13/308,951

(22) Filed: Dec. 1, 2011

(65) Prior Publication Data

US 2012/0075586 A1 Mar. 29, 2012

Related U.S. Application Data

(63) Continuation-in-part of application No. 13/033,930, filed on Feb. 24, 2011, now Pat. No. 8,534,839.

(60) Provisional application No. 61/309,209, filed on Mar. 1, 2010, provisional application No. 61/452,159, filed on Mar. 14, 2011.

(51) Int. Cl.
| | |
|---|---|
| *A61B 3/02* | (2006.01) |
| *A61B 3/00* | (2006.01) |
| *A61B 3/10* | (2006.01) |
| *A61B 3/028* | (2006.01) |
| *A61B 3/032* | (2006.01) |

(52) U.S. Cl.
CPC .............. *A61B 3/028* (2013.01); *A61B 3/032* (2013.01)
USPC ........................ 351/239; 351/246; 351/221

(58) Field of Classification Search
USPC .................................................. 351/239, 246
See application file for complete search history.

(56) References Cited

U.S. PATENT DOCUMENTS

| | | | |
|---|---|---|---|
| 2004/0075814 A1* | 4/2004 | Alster et al. .................. | 351/246 |
| 2008/0309880 A1* | 12/2008 | Fisher et al. .................. | 351/239 |
| 2009/0168020 A1* | 7/2009 | Ogilvie ......................... | 351/239 |
| 2010/0165294 A1* | 7/2010 | Barbur et al. ................. | 351/223 |

* cited by examiner

*Primary Examiner* — Mohammed Hasan
*Assistant Examiner* — Mustak Choudhury
(74) *Attorney, Agent, or Firm* — Haynes and Boone, LLP

(57) ABSTRACT

A system and method of testing vision performance includes displaying a visual recognition test to a subject and receiving from the subject a response to the visual recognition test. After receiving the response to the visual recognition test, a subsequent visual recognition test is selected based on the response received from the subject, the subsequent visual recognition test is displayed, and a response is received from the subject. The subsequent visual recognition tests are repeated until a predetermined criterion is reached. A vision performance score is determined based on the visual recognition tests displayed and the set of responses received from the subject and output from the system.

33 Claims, 5 Drawing Sheets

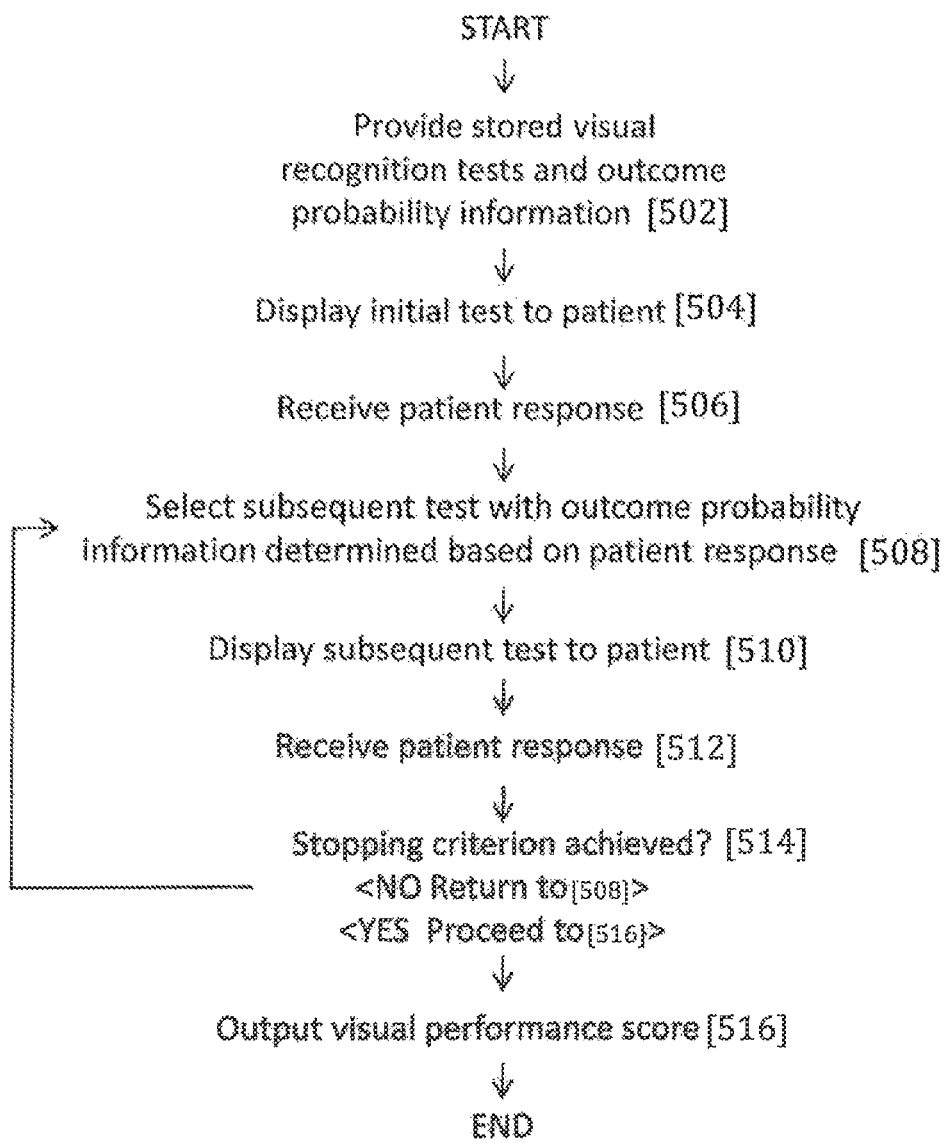

METHODS AND SYSTEMS FOR INTELLIGENT VISUAL FUNCTION ASSESSMENTS

RELATED APPLICATIONS

This application is a continuation-in-part of U.S. Ser. No. 13/033,930, filed Feb. 24, 2011 now U.S. Pat. No. 8,534,839, which claims priority to U.S. provisional application Ser. No. 61/309,209, filed on Mar. 1, 2010. This application also claims priority to U.S. provisional application Ser. No. 61/452,159, flied on Mar. 14, 2011. The contents of all of these related applications are herein incorporated by reference in their entirety.

FIELD OF THE INVENTION

The present invention relates to methods and systems for vision testing.

BACKGROUND OF THE INVENTION

Vision is traditionally tested by using a letter chart mounted on the wall 20 feet in front of a subject. The subject is asked to read the chart and assigned a vision score (often as a Snellen fraction such as 20/40). Normal vision is denoted as 20/20 (or 6/6 when metric units are used and the distance is 6 meters). Twenty feet (or 6 meters) is essentially infinity from an optical perspective. The Snellen score compares the distance the subject is able to see the target (20 feet, the numerator of the fraction) with the distance from which a normal seeing subject is able to identify the same target (40 feet or the denominator in the Snellen fraction).

LogMAR score (the logarithm of the minimum angle of resolution) is another commonly used scale. In this measurement system, the logarithmic Snellen scale is converted into a linear scale to measure visual acuity loss. 20/20 is converted to 0.0. Positive numbers indicate vision less than normal while negative numbers indicate better than normal visual acuity. LogMAR scores are more frequently used in scientific studies.

Greater accuracy in measuring a subject's ability to discern spatial differences can sometimes be achieved with other tests. For example, "vernier" acuity tests measure the ability to align two line segments. Contrast acuity measurement can also be useful. Typically, contrast acuity tests measure a subject's ability to discern a figure on a background under controlled illumination. Yet another known test of visual function is the "stereoscopic" acuity test, in which a subject is typically asked to detect an apparent depth difference between objects using both eyes.

For a long time clinicians have noted that subjects who score well on the standard vision tests continue to claim difficulties in vision. In other words, a subject is able to see 20/20 (LogMAR 0.0), but is not able to perform tasks that require normal vision. A clinical example would. be a patient who has cataracts and, although able to see well in a Doctor's office, is bothered by the glare of oncoming traffic at night. Such a condition can make the patient unable to drive at night—despite nominally "normal" vision.

Vision performance testing presents a number of challenges. While visual function is currently assessed in clinical and research settings by various measurements (e.g., visual acuity testing and contrast sensitivity testing), these measurements do not always provide an accurate indication of a subject's visual function in a practical sense. One drawback of these methods is that they typically test only one or two aspects of vision at a time (target size, percent contrast, and perhaps depth perception). Real world visual function consists of responding based on the multiple characteristics and simultaneous presentation of a visual target (e.g., size, percent contrast, motion or speed, color, etc.). Even if multiple individual visual tests are performed, each test is tailored to a specific aspect of vision, preventing a comprehensive assessment of vision performance from being obtained.

Even existing tests that attempt to evaluate visual function using representative activities of daily life have shortcomings. An example is testing vision performance using a driving simulator. The complexity of the apparatus often makes testing expensive, requiring subjects to travel to a particular location that may be remote from their physician's office. Additionally, the testing experience often includes tasks requiring more complex cognitive and physical function than simply vision. For example, in some driving simulators subjects must literally sit behind the wheel/windshield and operate controls in response to stimuli—this requires the coordination of visual processing and physical responses. Thus this testing scenario does not achieve a pure assessment of visual function.

Despite the currently available tests, there remains a need for vision performance measurements that are more consistent with real world function. Moreover, there is a need for intelligent testing systems that can help select the appropriate battery of tests for each subject and, in some instances, be able to modify the testing protocol in real time, based on initial testing results.

SUMMARY OF THE INVENTION

Methods and systems for intelligent visual function assessment are disclosed in which a variety of parameter files are provided to test vision. The parameter files can be stored as applications or program modules on a processor (e.g., a dedicated or general purpose computer or a remote server). The parameter files can include, for example, tests for monocular acuity, contrast sensitivity, and presentation time. Testing can initially employ a predefined sequence of the parameter files or a subset thereof. Alternatively, the system can provide controls, e.g., a graphical user interface (GUI), to allow a clinician to select parameter files and select the order or sequence of tests. The subject's responses can be analyzed in real time and, based on this analysis, the testing protocol can be modified or expanded. Following the testing, the processor can also provide an overall assessment based on known (or learned) patterns of responses. For example, a vision performance score can be determined using an item response theory (IRT) model.

In one aspect of the invention, a vision testing system is provided including a memory storing a plurality of parameter files defining a plurality of visual recognition tests, a display operable to display an image for each of the visual recognition tests to a subject, an input device operable to receive a response to each of the visual recognition tests from the subject, and a processor. The processor is operable to perform the following steps:

(a) display a visual recognition test from the parameter files to a subject;

(b) receive from the subject a response to the visual recognition test;

(c) select a subsequent visual recognition test from the parameter files based on the response from the subject;

(d) display the subsequent visual recognition test;

(e) receive from the subject a response to the subsequent visual recognition test;

(f) repeat steps (c)-(e) until a stopping criterion is achieved; and (g) output a vision performance score determined based on the set of responses received from the subject.

The processor can also display information about the progress of the testing to the operator through the operator's monitor.

The parameter files utilized by the vision testing system can contain a single visual recognition test, or a series of tests. The parameter files may contain tests designed to evaluate vision generally, or may contain a set of tests particularly designed to assess a particular aspect of vision. The parameter files, or a subset of a group of parameter files, can be linked to form a vision testing sequence that can be administered by the vision testing system. Further, a test supervisor can use the vision testing system to any of create, modify, delete, apply, link, and order a plurality of parameter files used to form a vision testing sequence.

In some embodiments, the parameter file can be automatically created by the processor prior to displaying a visual recognition test to the subject. To create the parameter file, the processor can select visual recognition tests for inclusion in the parameter file randomly or pseudo-randomly. In certain embodiments, any images corresponding to the visual recognition tests specified in the parameter files can be automatically created by the processor prior to displaying a first visual recognition test to the subject. In addition, once a parameter file is created, the processor can proceed through the visual recognition tests defined in the parameter file sequentially, or may select tests to display to a user randomly or pseudo-randomly. Further, the order of visual recognition tests can be updated dynamically during testing based on the responses received from the subject.

In order to allow the vision testing system to accommodate test supervisor monitoring and input, the system can, in some embodiments, include a second display operable to display a control panel including information regarding the visual recognition test displayed to the subject. The second display can include a graphical user interface (GUI) configured to allow a test supervisor to any of monitor and control the visual recognition test. In some embodiments, the (graphical user interface can allow the test supervisor to any of create, modify, delete, and apply parameter files using drag-and-drop operations.

Subject vision can be affected by a number of factors related to the display and surrounding environment. As a result, in some embodiments, the vision testing system can include a calibration sensor positioned in view of the display and configured to continually monitor one or more parameters of the testing environment (e.g., the display, the room illumination, etc., and as noted below). The calibration sensor can be further configured to produce an alert signal if the one or more parameters monitored by the sensor fall outside of an operating range. The operating range can he defined in a variety of manners. For example, the operating range can be defined as a range between a maximum and minimum parameter value. In other embodiments, the operating range can be defined by a target parameter value and an acceptable percentage variation from the target value.

The calibration sensor can be configured to monitor a variety of different parameters and, in certain embodiments, the one or more parameters monitored by the calibration sensor can include any of display contrast, display color, display luminance, display resolution, display brightness, and ambient illumination. Moreover, the vision testing system can be further configured to automatically adjust the one or more parameters of the display to maintain the one or more parameters within the operating range. In other embodiments, the vision testing system can be configured to prompt the test supervisor to adjust the one or more parameters of the display, and can. provide a control panel through the graphical user interface on the second display to allow adjustment of the one or more parameters.

To accommodate variation in the testing environment, the vision testing system can also be configured to adjust the visual recognition test on the display to account for a distance of the test subject from. the display. For instance, in some embodiments the vision testing system can be configured to accommodate testing distances between about 2 meters and about 9 meters. Adjusting the visual recognition test can be accomplished in a variety of manners, including, for example, adjusting any of the size, contrast, brightness, and time displayed for any image shown on the display.

The vision testing system of the present invention provides for testing vision performance in a variety of manners. For example, the processor can he configured to adjust the contrast of each visual recognition test by any of (i) fading a background color to match a foreground color, (ii) fading a foreground color to match a. background color, and (iii) fading both a foreground color and a background color to converge at a neutral color. As a result of the more refined and variable tests of vision performance, the vision testing system can determine a vision performance score with greater accuracy and precision. For example, in some embodiments, the vision testing system can he configured to output a vision performance score according to a $100^{th}$ (0.01) of a logMAR.

In some embodiments, various vision performance tests can be combined into a single visual recognition test. For example, the processor can be configured to test a plurality of vision parameters using a single visual recognition test by any of introducing and varying any of size, contrast, presentation time, movement, distracters, glare, color, crowding, retinal adaptation level, eccentricity, time to blink, and reaction time when displaying the visual recognition test to the subject.

After viewing an image associated with a visual recognition test on the display, a test subject can input a response using an input device. Various input devices can be utilized with the vision testing system of the present invention. For example, in some embodiments, the input device can include a button box having one or more buttons indicative of the orientations of targets presented on the display. In order to eliminate testing bias from subjects unfamiliar with the input device, the processor can be configured to administer an orientation test utilizing the display and input device prior to administering any visual recognition tests or vision testing sequence, as described above.

The processor of the vision testing system can also be configured to analyze responses received from the test subject and to compare those responses to responses received from previous subjects in order to recognize visual performance patterns. Such analysis can be conducted during or following administration of the visual recognition tests. In addition, in some embodiments, the processor of the vision testing system can be connected to additional memories via direct or networked connections such that the processor can exchange responses received from the subject with other data stored in the additional memories (e.g., other response sets collected from additional test subjects at other locations). All of these data can be used in analyzing the responses of a test subject to identify visual performance patterns that may be indicative of particular visual deficiencies and/or diseases. As part of the analysis, the vision testing system can be configured to create and output a three-dimensional representation of the visual performance of the subject using any of a variety of data metrics including any of response time, response accuracy, item difficulty, etc.

In another aspect of the invention, a method of testing vision performance is provided that can include selecting a first visual recognition test from a memory storing a plurality of parameter files, displaying an image to a subject, and varying one or more characteristics of the image to more accurately assess the visual performance of the subject. The method can further include receiving a response from the subject via an input device, selecting a subsequent visual recognition test from the memory based on the response of the subject, and repeating any of the steps above until a stopping criterion is achieved. Furthermore, the method can also include outputting a vision performance score determined based on the set of the responses received from the subject.

Any of the variations on the vision testing system discussed above can be incorporated into the provided method of testing vision performance. For example, the one or more characteristics of the image that can be varied can include any of the size of targets in the image, the contrast of the image, the presentation time, movement of targets in the image, the presence, number, and spacing of distractor elements in the image, the glare in the image, the color of the image, and the location of targets in the image. Each visual recognition test can be designed to test a variety of aspect of vision performance. In some embodiments, a visual recognition test can be selected to measure a particular vision performance criterion including any of retinal adaptation level, time to blink, and reaction time.

In addition, the method of testing vision performance can include any of the analysis techniques described above and can such analyses may be conducted during or following administration of the vision performance test. For example, outputting a vision performance score in the method described above can include displaying a three-dimensional representation of the vision performance of the test subject. As described above, the representation can be created using any of a variety of data metrics including any of response time, response accuracy, item difficulty, etc.

In particular embodiments of the present invention, software embodied in a computer-readable medium can be executable by a processor to cause the steps of such a method to be performed. In other embodiments, an adaptive visual performance testing system can include a memory storing a plurality of visual recognition tests, a display operable to display an image for each of the visual recognition tests to a subject, an input device operable to receive a response to each of the visual recognition tests from the subject, and a processor operable to execute instructions stored in the memory to perform the steps of such a method.

BRIEF DESCRIPTION OF THE FIGURES

A more complete understanding of the present invention and the advantages thereof may be acquired by referring to the following description, taken in conjunction with the accompanying drawings in which like reference numbers indicate like features.

FIG. 5 is a flow chart illustrating an exemplary method of testing vision performance according to a particular embodiment of the present invention.

DETAILED DESCRIPTION

Various embodiments of the disclosure are illustrated in the FIGURES, and like numerals are generally used to refer to like and corresponding parts of the various drawings. As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Further, unless expressly stated to the contrary, "or" refers to an inclusive or and. not to an exclusive "or."

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

Figure 1:
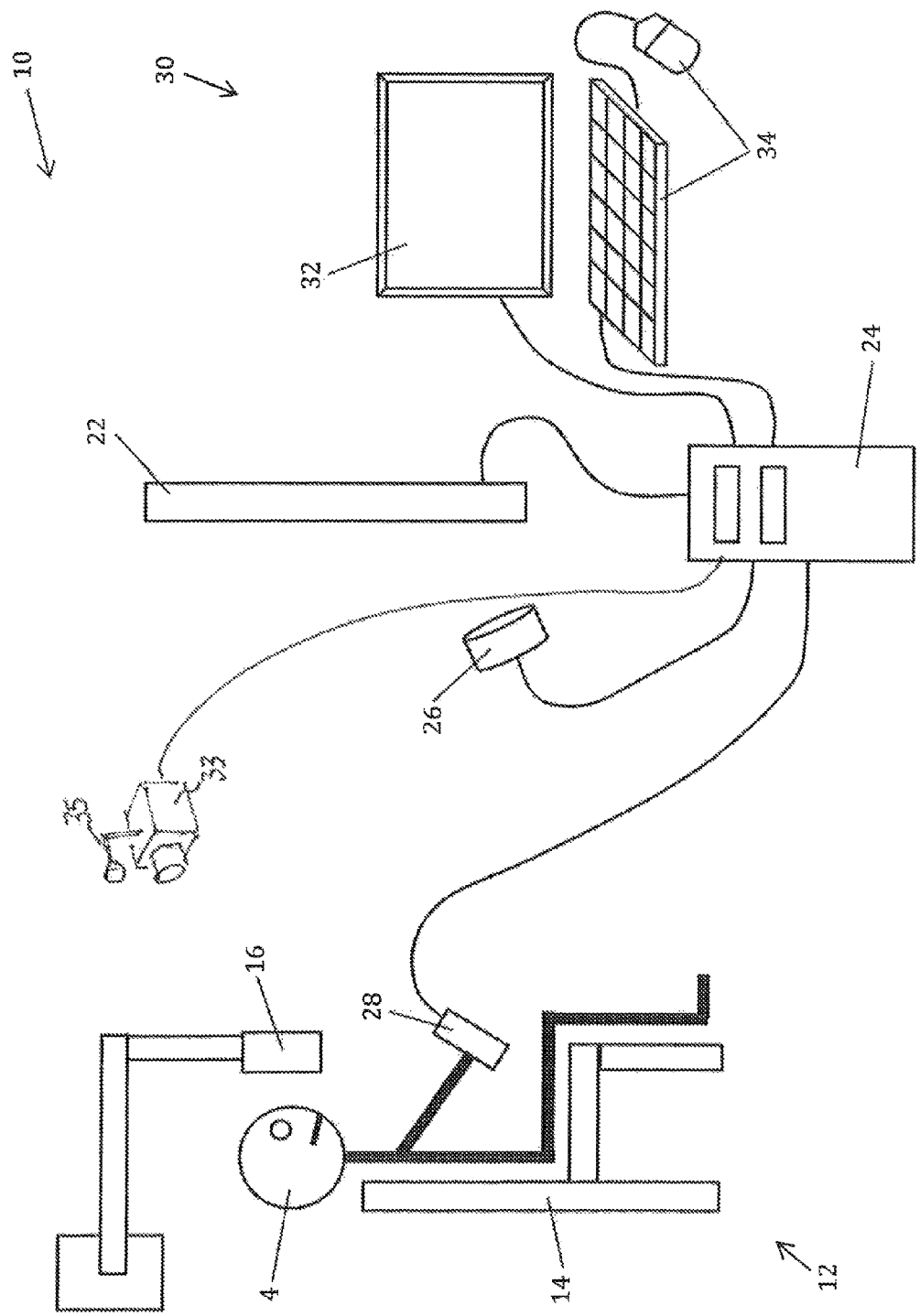
FIG. 1 is a schematic illustration of a vision testing system according to the invention.

FIG. 1 is a schematic illustration of a vision testing system 10 having a station 12 for placement of a subject 4. The station can include a chair 14 and a fixation. device 16. Fixation device 16 can include, for example, a chin rest and forehead rest to ensure that the subject remains in position at a fixed distance, e.g., 6 meters, from the test display 22. In certain embodiments, additional elements can be deployed, including a variety of visual aids (e.g., lenses of varying magnification power) to help test subject vision improvement using a visual aid.

The system can also include a processor 24 with associated memory or connections to other peripheral devices (not shown). The processor 24 can be a general purpose computer (e.g., a desktop personal computer) containing appropriate software to cause the computer to administer the vision testing system, or the processor can be a specifically tailored digital data processor designed for administering the vision testing system. The processor can be configured to perform any of a variety of tasks related to the administration of a vision performance test either during, or prior to, the initiation of such a test. For example, the processor can be configured to select a parameter file, or a series thereof, to create a vision testing sequence to administer to a test subject. Furthermore, the processor can he configured to create a parameter file from a set of visual recognition tests prior to displaying a visual recognition test to a user. The visual recognition tests included in a parameter file can be selected randomly or pseudo-randomly. The processor can also be configured to save computing resources during testing by creating any images corresponding to visual recognition tests specified in a parameter file prior to displaying a first visual recognition test to the subject. Still further, the processor can be configured to update the order of visual recognition tests dynamically during testing based on responses received from the test subject or commands input by a test supervisor.

The test display 22 connected to the processor 24 can be any of a variety of computer display devices. In some embodiments, the display 22 can be a large liquid crystal display (LCD) computer monitor (e.g., an LCD display having a diagonal measurement of 30 inches). Such a display provides ample space for displaying visual recognition tests including on-screen targets or objects of various sizes. Allowing for the variation of target size on the display allows the vision performance testing system to be utilized in a variety of testing environments, including environments where the test subject 4 may be at located at a variety of distances from the display 22. The processor 24 can be configured to adjust the visual recognition test to account for the distance between the test subject 4 and the display 22. In some embodiments, this distance can range between about 2 meters and about 9 meters. The distance of the test subject can be input into the vision testing system prior to the initiation of a vision performance test by the test subject 4 or a test supervisor (not shown).

A calibration sensor 26 can also be provided to ensure that the test display is maintained at a proper illumination level, and that other parameters of the display are held within an acceptable operating range. The calibration sensor 26 can be embodied in a variety of forms and placed at a variety of locations. In some embodiments, the calibration sensor 26 can be placed in view of the display 22 such that it can detect the illumination level of the display along with other operating parameters of both the display (e.g., display contrast, display resolution, display glare, display luminance, display color, display brightness, etc.) and the environment (e.g., ambient lighting, etc.). The calibration sensor 26 can be connected to the processor 24 such that the processor can read information from the calibration sensor to create a feedback loop with the display 22. That is, based on information gathered from the calibration sensor 26, the processor 22 can effect adjustments to one or more parameters of the display 22 to maintain the one or more parameters of the display within an acceptable operating range. An acceptable operating range may be denoted by a maximum acceptable parameter value and a minimum acceptable parameter value, or by a target parameter value and an acceptable percentage variation from the target value. Furthermore, should any of the parameters of the display fall out of the operating range, the processor 24 can also be configured to produce an alert signal. The processor 24 can produce an alert signal in a variety of manners, including, for example, displaying an alert message on the display 22 (or on a second display 32, which is discussed in more detail below) or sounding an audible alert for a test supervisor. In some embodiments, the system can also includes a video monitor 33 to evaluate the patient's ocular behavior (e.g., blinking or eye movements) as well as an additional optional infrared illumination light source 35 that may or may not be needed dependent upon testing conditions.

The system can further include an observer station 30 for a clinician, test proctor, or test supervisor to observe and/or control the vision testing system. The observer station 30 can include a second display 32 and one or more input devices 34, e.g., a keyboard or mouse. The second display 32 can display a control panel that includes information regarding the visual recognition test displayed to the subject. information regarding the visual recognition test can include an reproduction of the test image shown on the display 22, as well as other information including any of elapsed time, the correct answer, the parameter file containing the visual recognition test, the following visual recognition test (if selected), the previous visual recognition test and response, the subject's progress towards reaching a stopping criterion, etc.

Using the second display 32 and input devices 34, a test supervisor can, for example, any of create, modify, delete, link and order a plurality of parameter files or individual visual recognition tests to form a vision testing sequence. The vision testing system can accommodate this control via the inclusion of, for example, a graphical user interface (GUI) that allows the test supervisor to any of create, modify, delete, and apply any of various parameter files using, for example, drag-and-drop operations. Such an interface can allow the test supervisor to monitor or control the vision performance test and, if desired, assume the duties of the processor in selecting visual recognition tests or parameter files to be used in creating a vision testing sequence to be administered to the test subject.

The processor 24 can receive responses to visual recognition tests via a testing input device 28. Testing input device 28 can be any of a variety of devices similar to input devices 34. In some embodiments, testing input device 28 can be a purpose-built controller suitable to be held by a test subject 4 and including, for example, input buttons (shown in FIGS. 3A and 3B) that correspond to potential responses to a visual recognition test. Testing input device 28 can be connected to processor 24 wirelessly or via a wired connection (e.g., universal serial bus or USB). In some embodiments, a testing input device having a simple layout is preferred to prevent a test subject 4 from having to move away from fixation device 16 in order to see what input button he or she is selecting.

Figure 2:
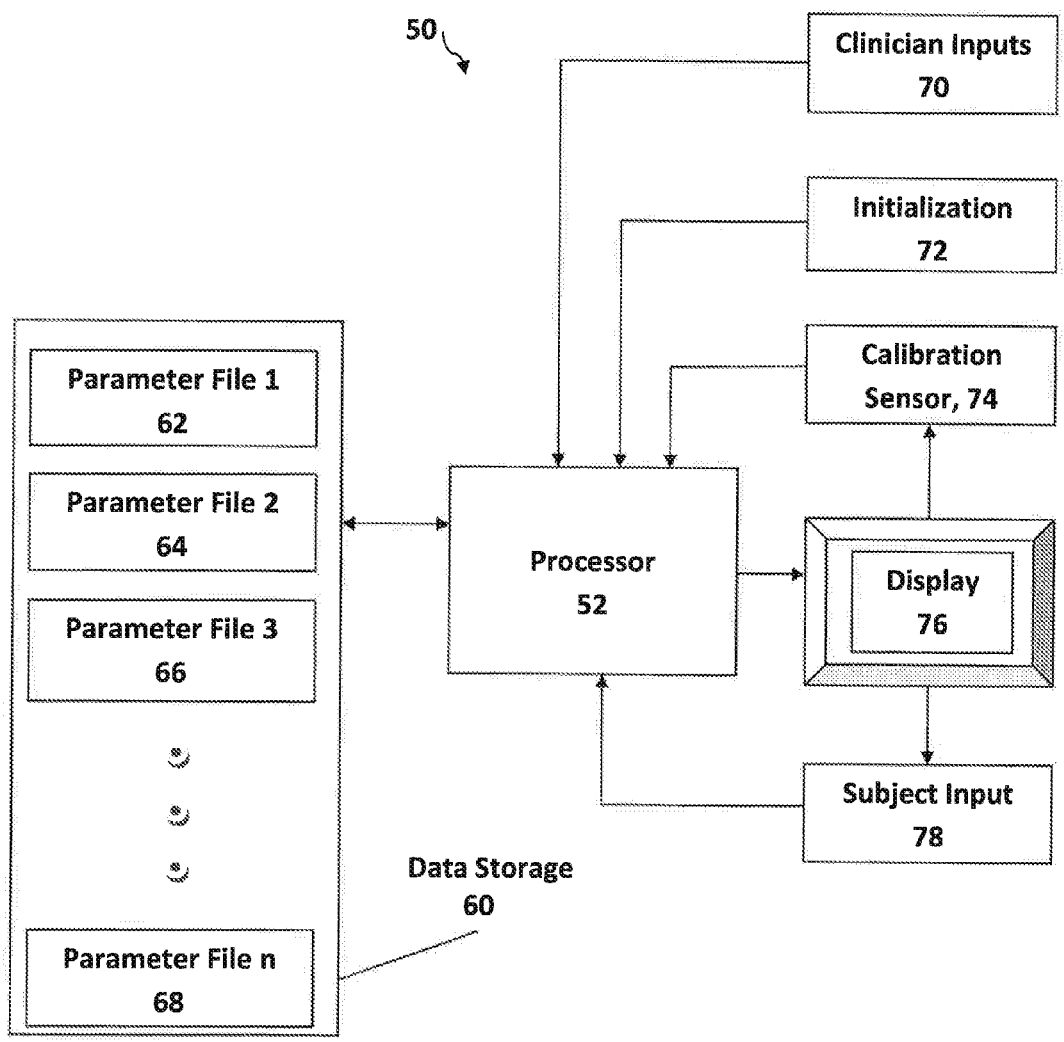
FIG. 2 is a block diagram of certain components of a vision testing system according to the invention.

FIG. 2 is a block diagram of certain components of a vision testing system 50 according to the invention. At the center of FIG. 2 is processor 52 (similar to processor 24 in FIG. 1 described above), which includes appropriate software to configure processor 52 to administer the vision testing system of the present invention. Prior to the administration of a vision performance test, processor 52 can receive initialization data 72. Initialization data 72 can include a variety of testing parameters and other information, including, for example, the distance of a test subject from the display 76, the ambient level of illumination, the testing subject name or other identifying information, a parameter file or vision testing sequence (e.g., a string of parameter files) for use in the vision performance test, etc.

Processor 52 can also be configured to receive information from calibration sensor 74 regarding the testing environment and display 76. As discussed above, processor 52 can be configured to automatically adjust one or more parameters of the display 76 in response to information received from the calibration sensor 74, or can produce an alert to prompt a test supervisor for corrective action.

To begin a vision performance test, processor 52 can access, for example, connected data storage memory 60 which includes one or more parameter files 62, 64, 66, and 68 that define a plurality of visual recognition test. Data storage memory 60 can be any directly or network connected digital memory store. Processor 52 can read the one or more parameter files and display associated visual recognition tests on display 76 during the test, or can be configured to create any images associated with a visual recognition test before test administration, as discussed above.

Once a visual recognition test is shown on display 76, processor 52 can be configured to wait for a response in the form of subject input 78. A variety of subject input 78 can be collected during a vision performance test. In some embodiments, received subject input can be in the form of a signal or other indication of an orientation (e.g., up, down, left, right, and combinations thereof) that correspond to an orientation of a target shown on display 76 (e.g., the direction of the open end of a letter "C" displayed on the display 76). Processor 52 can. analyze the subject input 78 in connection with information about the visual recognition test shown on the display 76 to determine, for example, the accuracy of the subject input, the response time, the difficulty of the visual recognition test, etc. This analysis can aid processor 52 in selecting additional visual recognition tests from the parameter file (or additional parameter files in the vision testing sequence) for presentation to the test subject to better assess their vision performance. As discussed above, these dynamic changes to the vision testing sequence can be taken by the processor 52 based on its analysis of the subject input 78 and data in the data storage memory 60, or can be received through clinician inputs 70 (e.g., through the graphical user interface and second display 32 discussed above).

The visual recognition tests defined by the parameter files 62, 64, 66, 68 in data storage memory 60 can take advantage of the display 22, 76 to test vision in ways that are not possible with traditional printed eye charts. For example, the processor can be configured to adjust the contrast of an image associated with a visual recognition test in a variety of manners. For example, the processor can adjust the contrast of the image shown on the display 22, 76 by any of fading a background color to match a foreground color, fading a foreground color to match a background color, and fading both a foreground color and a background color to converge at a neutral color. This fading can be accomplished in a single image by adjusting the contrast as the test subject views the image, or can be adjusted by showing the test subject a series of images at varying contrast levels throughout the course of the vision performance test.

In addition, the display 22, 76 can be controlled to vary a number of other parameters of any image associated with a visual recognition test. These can include, for example, the size of any target in an image, the presentation time of the target or image, the movement of any targets in an image, any distractor elements in the image, the glare of the image, the crowding of elements in the image, and the eccentricity of elements in the image. These variations can be introduced individually, or in combinations, to one or more images associated with one or more visual recognition tests to assess general vision performance, or to assess particular aspects of vision performance such as retinal adaptation level, time to blink, reaction time, etc.

Figure 3A:
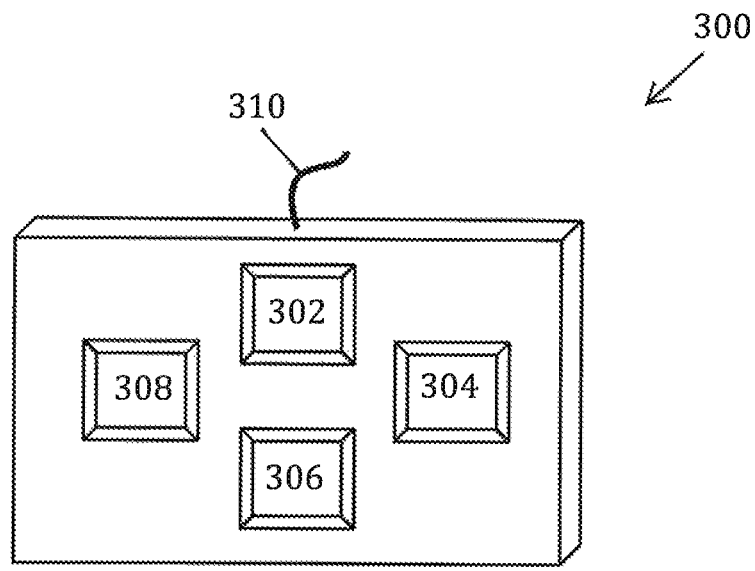
FIG. 3A is a schematic illustration of a subject input device according to the invention.

FIG. 3A is a schematic illustration of a subject input device 300 according to the invention. A test subject can use a device like input device 300 to provide processor 24, 52 with subject input 78, as discussed above. In the illustrated embodiment, input device 300 is a generally rectangular controller having four input buttons 302, 304, 306, 308, along with a wired connection 310 to connect to processor 24, 52. In some embodiments, visual recognition tests displayed to a test subject may include variations on the Landolt C, where a test subject is asked to indicate the orientation of a "C" shown on the display 22, 76. Thus, for example, if a user were shown a Landolt C as it appears on this page, the user should press input button 304 to indicate that the "C" points to the right.

Figure 3B:
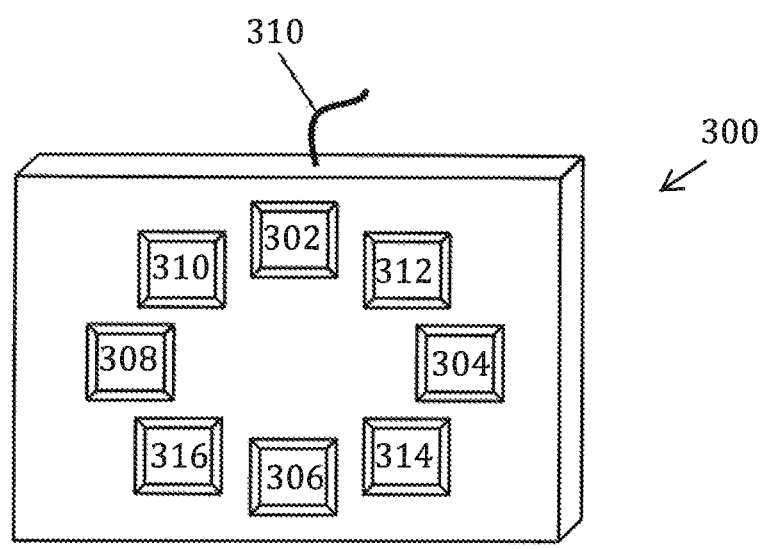
FIG. 3B is a schematic illustration of an alternative embodiment of a subject input device according to the invention.

In other embodiments, the vision testing system may employ an input device 300 like that shown in FIG. 3B. The input device of FIG. 3B is substantially similar to the device illustrated in FIG. 3A, but includes additional diagonal input buttons 310, 312, 314, 316. These additional directional buttons allow more variation in, for example, a Landolt C test, because the C can be oriented in any of eight directions rather than 4.

In order to ensure that a test subject understands how to use the input device 300 and other components of the vision testing system 10, the processor can be configured to administer an orientation test prior to administering any vision performance test. The orientation test can include, for example, a series of visual recognition tests similar to those administered during the vision performance test, but during the orientation test the display can alert the test subject as to the correct answer and corresponding input button that should be pressed. After a test subject successfully passes the orientation test, the vision testing system can proceed to administer the vision performance test as discussed above.

Following administration of the vision performance test, the processor can be configured to conduct one or more analyses of the test results. For example, the processor 24, 52 can be configured to analyze responses received from the test subject and compare those responses to responses received from previous subjects to recognize a visual performance pattern. The visual performance pattern can correspond, for example, to a particular visual deficiency or disease (e.g., myopia, cataracts, etc.). In addition, the processor 24, 52 can be configured to access additional connected memories via direct or networked connections such that the processor can exchange responses received from the test subject with other data. In this way, a network of vision testing systems can compare test subject responses with a large data set of other responses in order to more accurately identify visual performance patterns. Additionally, the processor can be configured to compare an individual subject's results to their own previous results to allow a higher degree of sensitivity to detect changes in visual function.

Based on all or any subset of these data, the vision testing system can output a vision performance score to quantify the vision performance of the test subject. As a result of the finer control over visual recognition tests displayed to a test subject, the vision testing system of the present invention can more precisely and accurately assess the vision performance of the test subject. For example, the vision testing system can output a vision performance score to a $100^{th}$ (0.01) of a logMAR. (as compared to more commonly used visual tests that are unable to determine visual ability to a similar degree of sensitivity). In addition, the vision testing system can create additional forms of a vision performance score to aid test subjects and medical professionals in assessing and treating visual impairments. For example, the vision testing system can create a three dimensional (or four dimensional, five dimensional, etc.) representation of the visual performance of the test subject. Any of a variety of collected data can be used in forming the representation, including any of response time, response accuracy, test difficulty, etc.

Figure 4:
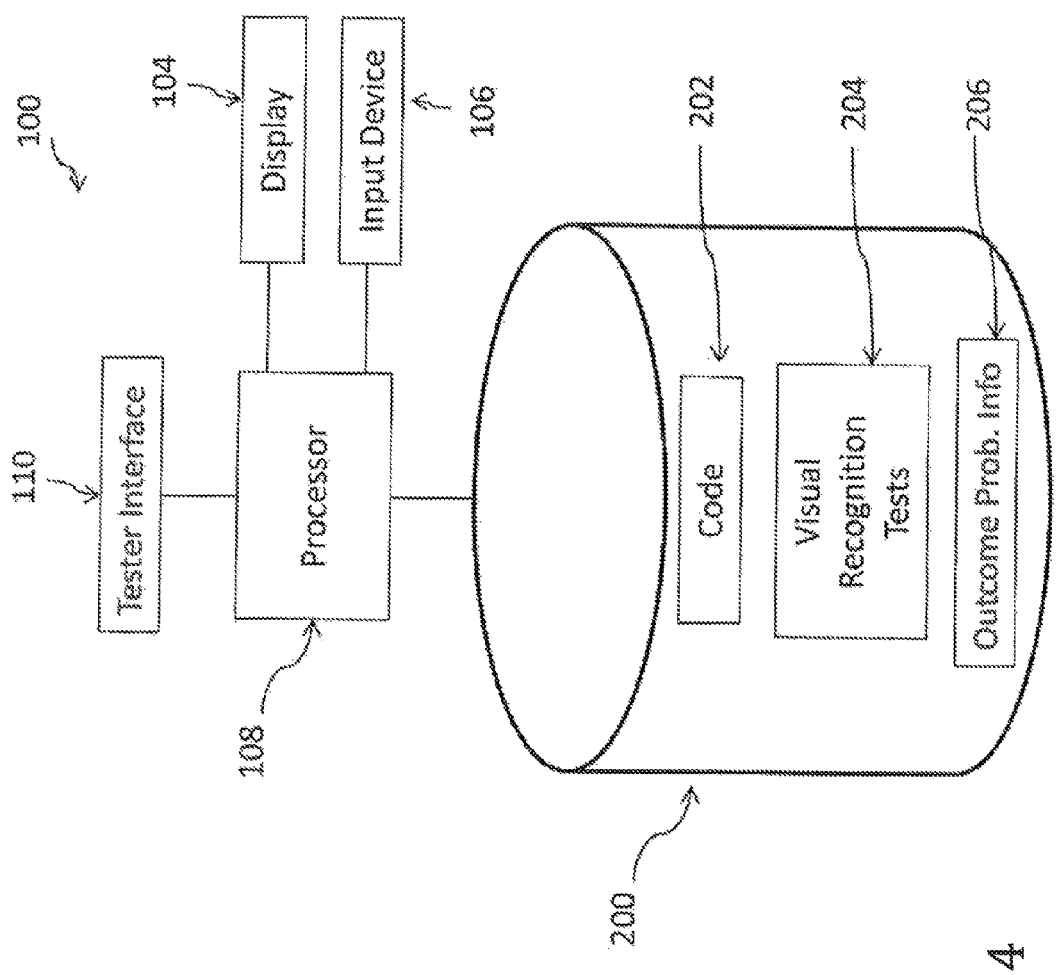
FIG. 4 is block diagram of another adaptive vision testing system according to a particular embodiment of the present invention.

FIG. 4 is a block diagram of a visual performance testing system 100 according to another embodiment of the present invention. The system 100 includes a subject interface comprising a display 104 and an input device 106. The display 104 may be any suitable means for producing a visually perceptible image for a subject, such as a monitor. The input device 106 includes one or more components suitable for receiving responses from a subject, such as a push button, a keyboard, a mouse, or any other suitable input device. A timer may also be associated with the input device 106 so that the time interval required for the subject to provide a response can be measured. In various embodiments, the system 100 may include multiple input devices for receiving different forms of response from the subject.

The system 100 also includes a processor 108 and a memory 200 that stores instructions executable by the processor, hereinafter referred to as "code" 202. The memory 200 may include any suitable form of information storage, whether volatile or non-volatile, including but not limited to electronic, magnetic, or optical memory. The processor 108 may include one or more microprocessors, microcontrollers, programmable devices, or other suitable components for processing information and executing instructions to cause various functions of the system 100, including any of those functions described herein, to be performed. In particular, the processor 108 can generate an output at a tester interface 110 of a visual performance score for the subject. The output can be produced in any suitable format for the tester interface 110, including a visual display on a monitor, a paper printout, colored lights, audible reports generated by a speech synthesizer, or other output methods known to those skilled in the art. The processor 108 may also receive selections of output format through the tester interface 110, as well as other information allowing the user to control the operation of the system 100.

The memory 200 also stores information pertaining to a set of visual recognition tests 204 and associated outcome probability information 206 for each of the visual recognition tests 204. The outcome probability information 206 can be collected using statistically controlled analysis of subject responses, for example. In various embodiments of the present invention, the visual recognition tests 204 provide a visually perceptible image to a subject using the display 104, and the subject provides a suitable response using the input device 106. In this context, "recognition" can refer to any suitable subject response to the display of the image. For example, the subject can be tested to determine whether he can distinguish the image at all. In another example, the subject can be asked to distinguish between a number of alternatives, such as identifying the color, shape, or orientation of the object. Commonly used images known in the art of visual testing include the orientation of a letter "E" or a Landoll C, wherein the subject indicates the orientation of the image (up, down, left, right) using a four-key pad (e.g., the key pad 300 shown in FIG. 3A) as the input device 106.

In particular, the visual recognition tests 204 may advantageously be designed to vary an image parameter affecting the probability of visual recognition, which is in turn used to assign outcome probability information 206 to the test 204. Using responses from a wide range of visual abilities of subjects, the outcome probability information 206 of each test may be estimated. For example, smaller objects are ordinarily more difficult to distinguish than larger objects, so a test 204 that requires the subject to recognize an object when it is seen and to respond within a certain time period will be made more difficult by using smaller images. Alternatively, the time period for presentation of the image may be varied to alter the difficulty of the task. Image parameters can be varied within the test 204 or between tests 204. In one example of the former type of test 204, an image can begin at a small size and can be enlarged over time, and the subject's success at recognition is assessed based on the time at which the subject recognizes the image. In an example of the latter, different visual tests 204 can display the same image at different sizes, and the subject's success at recognition can be assessed based on whether the image of a particular size is recognized by the subject.

The visual recognition tests 204 can also advantageously vary a number of different image parameters that affect the difficulty of image recognition and therefore, may optimally distinguish levels of visual ability. For example, image parameters such as target contrast, target size, color, and rate of motion can be varied along with image size. Advantageously, the algorithm used for the display 104 can allow image parameters to be systematically varied to modify these image parameters, and a high-resolution display 104 can be used to enable finer measurements of contrast variation and the like. Additional visual effects, such as the presence of distractors or glare in the image, can also be evaluated for their effects on visual performance. Particular embodiments of the present invention can advantageously use the outcome probability information 206 across tests 204 varying a number of different image parameters and the response vectors to determine an overall visual performance score that provides a more holistic indication of visual performance for a variety of different visual recognition tasks that are performed in daily life. As noted previously, the user may also be allowed to customize the testing process, including the selection of particular visual recognition tests 204, using the tester interface 110.

Various embodiments of the present invention employ an adaptive testing procedure, which is to say that subsequent visual recognition tests 204 given to the subject are determined based on the subject's performance on a previous visual recognition tests 204. In particular, subsequent tests 204 can be chosen at an appropriate level of outcome probability information 106 based on the subject's current estimated ability. Thus, for example, a test 204 with comparable outcome probability information 206 but using a different visual recognition task could be selected. In another example, a visual recognition test 204 could be selected with outcome probability information 206 to better match a subject's current estimated ability if the subject did not successfully respond to the previous visual recognition test 204. This adaptive gradation of outcome probability information 206 allows testing to include tests that are appropriate to each subject's level of ability, so that the subject is not given a large number of tasks that are too difficult or too easy given the current estimate of ability level. Therefore, the adaptive testing process allows the subject's visual performance to be tested efficiently and in a way that may provide a better overall indication of the subject's visual function in daily activities.

The visual performance score can be determined based on the responses to the tests 204 and the outcome probability information 206 of the tests 204 when a predetermined number of responses have been received. In particular examples, the score can be determined for multiple tasks having different difficulty levels using an item response theory (IRT) scoring algorithm. In its simplest form, the Rasch equation gives a probability of success (also called item response function) for a person having a certain level of ability as follows:

$$p_{ij}(\theta_j) = \frac{1}{1 + e^{(\theta_j - b_i)}}$$

wherein $p_{ij}(\theta_j)$ is a probability of success for a person of ability $\theta_j$ to correctly respond to an item of difficulty $b_i$.

The equation can be further modified for tasks that may not be equa. discriminatory among abilities, where a is the degree to which a task discriminates between people with different ability levels, as follows:

$$p_{i,j}(\theta_j) = \frac{1}{1+e^{a_i(\theta_j - b_i)}}$$

The probability of correctly guessing an answer can further be incorporated into the equation as a guessing parameter c:

$$p_{ij}(\theta_j) = c + \frac{(1-c)e^{a_i(\theta_j - b_i)}}{1+e^{a_i(\theta_j - b_i)}}$$

Ability can be estimated using item response functions that consider both the item parameters and the subject's set of correct and incorrect responses. This information can also be used in the adaptive test selection process to estimate visual performance more efficiently and to further improve reliability of the performance score. Such techniques are known in cognitive testing, such as the adaptive testing used in standardized college admission tests, but the application to visual performance testing and the evaluation of characteristics (e.g., difficulty, discrimination) for visual recognition tasks is not found in conventional testing. On the contrary, considerable effort is devoted in cognitive testing to overcoming difficulties in visual performance so that even people with visual impairments can be adequately tested for cognitive ability.

FIG. 5 is a flow chart 500 showing an example method for testing visual performance according to a particular embodiment of the present invention. At step 502, a memory is provided with a plurality of visual recognition tests and associated outcome probability information for each test. At step 504, one of the visual recognition tests is displayed to a subject. At step 506, a response is received from the subject.

After the response is received, the method proceeds to step 508, wherein a subsequent visual recognition test is selected to have outcome probability information determined based on the subject's response. The selected visual recognition test is then displayed to the subject at step 510, and a response is received from the subject at step 512. In decision step 514, a determination is made of whether a stopping criterion has been achieved. For example, stopping criteria could include reaching a predetermined number of responses, achieving a predetermined level of statistical significance in the responses, or other similar standards for determining when the information collected. adequately indicates the subject's visual performance. The stopping criterion may also be a combination of such standards, so that the stopping criterion is considered to be achieved when each of the standards is achieved, when a total score based on all of the standards is reached, etc. If the stopping criterion is achieved, then steps 508, 510, and 512 can be repeated until enough responses are received.

Once the predetermined number of responses is received, an output including a visual performance score determined from the responses and the outcome probability information of the visual recognition tests is generated at step 516. In particular embodiments, the visual performance score can be a single numerical rating or "pass/fail" output. In alternative embodiments, the visual performance score can include separate scores for different visual tasks as well. In general, any suitable form of scoring output that takes into account responses collected during adaptive testing with varying outcome probability information would be consistent with the present invention.

The vision testing system and method of the present invention provide unique benefits and capabilities over prior vision testing systems. In summary, these can include:
1. Parameter file controlling targets—the use of a specific and dedicated list of target instructions and ordered testing parameters.
2. Randomization and automated creation of parameter files—dedicated computer software with GUI interface that allows proctor to create, modify, and apply parameter files.
3. Targets created in advance of run-time—all visual targets needed for system use are created, based on parameter file, or other specification, in advance allowing for efficient and timely presentation to test subject.
4. Automatic calibration of contrast level of monitor—system of pre-designed automatic steps as well as hardware that ensures proper calibration of all testing system physical parameters, including, but not limited to, color, luminance, testing distance, screen resolution, brightness, ambient room illumination, etc.
5. Monitoring of screen luminance calibration with ability to signal if calibration drifts off by a pre-specified amount (which can be user-settable)—this ensures that all testing is done under proper conditions at all times, making it reliable and accurate.
6. Ability to test at a variable range of testing distances—testing can be done at any distance between, for example, about 2 meters and about 9 meters.
7. Ability to display contrast in three different ways—fade to foreground, fade to background, and fade to middle between background and foreground.
8. Variable target size ability—enabling testing to a $100^{th}$ (0.01) of a logMAR rather than what is used in traditional Snellen-based charts.
9. GUI interface to allow drag and drop control of main system and parameter file/target generation.
10. Combination of multiple parameters simultaneously into vision testing targets—prior systems test each parameter independently while this system allows the ability to combine any number of chosen parameters for target presentation.
    a. These include, but are not limited to, size, contrast, presentation time, movement of target, distracters, glare, color, crowding, retinal adaptation level, eccentricity, time to blink (or other event), reaction time, etc.
11. Input via remote access device—can be a custom-built input device/button box that can be used for test subject interaction with vision testing system.
12. Separate test and control screens allowing proctor to monitor subject responses—this allows the proctor to control and monitor in real time testing system functions while the test subject is undergoing testing.
13. Algorithm to ensure subject is able to correctly interact with vision testing system before being tested—specifically designed set of targets used to ensure that the test subject is able to correctly identify targets and interact with the system. The test subject must successfully pass this portion of the test in order to continue with clinical testing. The test supervisor or proctor can elect to skip this section at their discretion as a supervisor option.
14. Ability to link multiple parameter files to create a fluid vision testing sequence—the proctor or test supervisor can interact with the system and select multiple parameter files to be used and presented in a pre-determined sequence to facilitate testing efficiency.

15. Ability to either test subject via pre-determined set of targets (parameter files) or to allow the vision testing system to determine which target to present—the testing supervisor can choose which targets to present to the test subject via the parameter files or can allow the system to intelligently choose targets for presentation on the go. Note that the system can intelligently create and choose parameter files (in addition to individual targets) in advance of the vision performance test or dynamically during the test.
16. Targets presented by algorithm to both measure overall function as well as probe in detail different areas of weakness in different subjects depending on results received during the test—using a method of self-learning (artificial intelligence, or AI), the system is able to determine which targets to present based on the test subject's previous responses and past knowledge of other responses received from previous test subjects.
17. Artificial Intelligence (AI) to allow the system to learn patterns of responses and group response patterns into disease patterns—the system is designed to learn by experience and develop clusters of similar responses of previous test subjects who may have a particular clinical entity. A probability estimate for the association of the current test subject and the previously established clusters can be reported as, or in association with, the vision performance score.
18. Calculation of art Item Response Theory (IRT) score based on target difficulty—using standard public domain algorithms an item response score or propensity score can be calculated based on the test subject's responses.
19. Creation of a 3D graphical rendering of the test subject's vision performance—results of the test subject's responses can be displayed in a three-dimensional graphical rendering to highlight the test subject's vision performance. Additionally, the IRT score as well as several other statistical indices can be displayed that convey how the test subject's responses differ from normal responses or prior testing of that particular test subject.
20. Calculation of the difference between the test subject's responses and normal responses with statistical analyses of the differences. Additional ability to compare two different test subjects' results to each other, as well as to a normal or other sample of a population.
21. Ability of system to review error profile and determine similarities or differences in wrong answers among groups—in addition to analysis of correct test subject responses, the system has the ability to perform an error analysis on a test subject's incorrect responses to identify patterns that are capable of defining a disease or other clinical entity.
22. Additional option of networking multiple systems together to allow greater sensitivity in AI testing and grouping of subjects—in order to leverage the intelligent aspects of the system, each independent system can be linked electronically to share system experience and create greater power and efficiency in both testing and analysis methods.
23. Ability to compare results from multiple sites and combine results since test experience for each test subject is identical (or controlled for by testing variation to account for different distances, ambient illumination, etc.)—leveraging the ability to ensure constant testing conditions through the above method, all results from the system are comparable and combinable for the purposes of data collection and analysis.
24. Use of a "fixation target" to prompt the subject that a test target is coming and to be "looking at the screen."
25. Monitoring a subject's ocular status throughout the testing period, e.g., to detect ocular movement away from the target as well as any blinks, and determine if a blink has affected the subject's ability to answer the target properly. Also, the blink monitor can be used to time the target presentations in relation to a subject's blink—e.g., present a target 50 milliseconds after the subject blinks.
26. Using additional light sources that do not affect the subject's ability to view the target but allow for a greater ability to employ video monitoring of the subject's eye being tested (e.g., an IR (infrared) light source aimed a the subject).

Although embodiments have been described in detail herein, it should be understood that the description is by way of example only and is not to be construed in a limiting sense. For example, while a particular example of a testing method has been presented, it should be understood that the testing method could also be modified in a manner consistent with any of the various test selection methods and image parameter variations described. herein. It is to be further understood, therefore, that numerous changes in the details of the embodiments and additional embodiments will be apparent to, and may be made by, persons of ordinary skill in the art having reference to this description. It is contemplated that all such changes and additional embodiments are within scope of the claims below and their legal equivalents.

The invention claimed is:

1. A vision testing system, comprising:
   a memory storing a plurality of parameter files defining a plurality of visual recognition tests;
   a display operable to display an image for each of the visual recognition tests to a subject;
   an input device operable to receive a response to each of the visual recognition tests from the subject;
   a calibration sensor positioned in view of the display and configured to continually monitor one or more parameters of the display during the visual recognition tests;
   a processor operable to execute stored instructions to cause the following steps to be performed:
   (a) display a visual recognition test from the parameter files to a subject;
   (b) receive from the subject a response to the visual recognition test;
   (c) select a subsequent visual recognition test from the parameter files based on the response from the subject;
   (d) adjust at least one of the parameters of the display in response to at least one of the selection of the subsequent visual recognition test and at least one of the parameters of the display being outside of an operating range as indicated by the calibration sensor;
   (e) display the subsequent visual recognition test;
   (f) receive from the subject a response to the subsequent visual recognition test;
   (g) repeat steps (c), (e), and (f) until a criterion is achieved; and
   (h) output a vision performance score determined based on the set of responses received from the subject.

2. The vision testing system of claim 1, wherein the parameter files or a subset thereof can be linked to form a vision testing sequence.

3. The vision testing system of claim 2, wherein a test supervisor is able to any of create, modify, delete, apply, link, and order the plurality of parameter files used to form the vision testing sequence.

4. The vision testing system of claim 2, wherein the parameter file is automatically created by the processor prior to displaying a visual recognition test to the subject.

5. The vision testing system of claim 4, wherein the processor selects the visual recognition tests to display to a user randomly or pseudo-randomly.

6. The vision testing system of claim 4, wherein any images corresponding to the visual recognition tests specified in the parameter file are automatically created by the processor prior to displaying a first visual recognition test to the subject.

7. The vision testing system of claim 1, wherein the order of visual recognition tests is updated dynamically during testing based on responses received from the subject.

8. The vision testing system of claim 1, further comprising a second display operable to display a control panel including information regarding the visual recognition test displayed to the subject.

9. The vision testing system of claim 8, wherein the second display includes a graphical user interface (GUI) configured to allow a test supervisor to any of monitor and control the visual recognition test.

10. The vision testing system of claim 9, wherein the GUI allows the test supervisor to any of create, modify, delete, and apply parameter files using drag-and-drop operations.

11. The vision testing system of claim 1, wherein the calibration sensor is further configured to monitor ambient lighting of the testing environment.

12. The vision testing system of claim 11, wherein the one or more parameters monitored by the calibration sensor include any of display contrast, display color, display luminance, display resolution, display brightness, and ambient illumination.

13. The vision testing system of claim 11, wherein the vision testing system is further configured to automatically adjust the one or more parameters of the display to maintain the one or more parameters within the operating range.

14. The vision testing system of claim 11, wherein the operating range is represented by a target parameter value and an acceptable percentage variation from the target parameter value.

15. The vision testing system of claim 1, wherein the processor is further configured to adjust the visual recognition test on the display to account for a distance of the test subject from the display.

16. The vision testing system of claim 15, wherein the distances is between about 2 meters and about 9 meters.

17. The vision testing system of claim 1, wherein the system further comprises a camera for monitoring the subject during testing.

18. The vision testing system of claim 17, wherein the system further comprises an illumination source.

19. The vision testing system of claim 18, wherein the illumination source further comprises a source on non-visible light.

20. The vision testing system of claim 17, wherein the camera is a video camera.

21. The vision testing system of claim 1, wherein the processor is further configured to adjust the contrast of each visual recognition test by any of:
fading a background color to match a foreground color;
fading the foreground color to match the background color; and
fading both the foreground and the background colors to converge at a neutral color.

22. The vision testing system of claim 1, wherein the processor is further configured to output a vision performance score according to a 100th (0.01) of a logMAR.

23. The vision testing system of claim 1, wherein the processor is further configured to test a plurality of vision parameters using a single visual recognition test by any of introducing and varying any of size, contrast, presentation time, movement, distracters, glare, color, crowding, retinal adaptation level, eccentricity, time to blink, and reaction time when displaying the visual recognition test to the subject.

24. The vision testing system of claim 1, wherein the input device comprises a button box including one or more buttons indicative of target orientations presented on the display.

25. The vision testing system of claim 1, wherein the processor is further configured to, prior to performing steps (a)-(g), administer an orientation test utilizing the display and input device.

26. The vision testing system of claim 1, wherein the processor is further configured to analyze responses received from the subject and compare those responses to responses received from previous subjects to recognize a visual performance pattern.

27. The vision testing system of claim 26, wherein the processor is further configured to create and output a three-dimensional representation of the visual performance of the subject.

28. The vision testing system of claim 26, wherein the processor is connected to additional memories via direct or networked connections such that the processor can exchange responses received from the subject with other data.

29. A method of testing vision performance, comprising:
selecting a first visual recognition test from a memory storing a plurality of parameter files;
displaying an image to a subject;
monitoring one or more parameters of the display during the visual recognition tests with a calibration sensor;
varying one or more characteristics of the image to more accurately assess the visual performance of the subject;
receiving a response from the subject via an input device;
selecting a subsequent visual recognition test from the memory based on the response of the subject;
adjusting at least one of the parameters of the display in response to at least one of the selection of the subsequent visual recognition test and at least one of the parameters of the display being outside of an operating range as indicated by the calibration sensor;
repeating the steps of varying the one or more characteristics of the image, receiving the response from the subject, and selecting the subsequent visual recognition test from the memory until a criterion is achieved; and
outputting a vision performance score determined based on the set of responses received from the subject.

30. The method of claim 29, wherein the one or more characteristics of the image varied include any of size of targets in the image, contrast of the image, presentation time, movement of targets in the image, the presence, number, and spacing of distractor elements in the image, glare on the image, color of the image, and location of targets in the image.

31. The method of claim 29, wherein a visual recognition test is selected to measure particular vision performance criteria including any of retinal adaptation level, time to blink, and reaction time.

32. The method of claim 29, wherein outputting a vision performance score comprises displaying a three-dimensional representation of the vision performance of the subject.

33. The method of claim 29, wherein the method further comprises using a fixation mechanism to aid in subject attentiveness.

\* \* \* \* \*